United States Patent [19]

Bourne et al.

[11] Patent Number: 6,011,183
[45] Date of Patent: Jan. 4, 2000

[54] PROCESS FOR PREPARING ORGANIC HYDROPEROXIDES

[75] Inventors: Stephen William Bourne; Pieter Oldenhove, both of Amsterdam, Netherlands

[73] Assignee: Shell Oil Company, Houston, Tex.

[21] Appl. No.: 09/191,914

[22] Filed: Nov. 13, 1998

[30] Foreign Application Priority Data

Apr. 13, 1997 [EP] European Pat. Off. .............. 97309150

[51] Int. Cl.[7] ................................... C07C 409/02
[52] U.S. Cl. ........................... 568/571; 568/568; 568/570
[58] Field of Search .................... 568/568, 570, 568/571

[56] References Cited

U.S. PATENT DOCUMENTS

| | | | |
|---|---|---|---|
| 2,798,096 | 7/1957 | Baumgartner | 568/571 |
| 3,816,540 | 6/1974 | Barone et al. | 260/610 B |
| 4,329,514 | 5/1982 | van der Weijst et al. | 568/577 |
| 4,404,406 | 9/1983 | Lutz et al. | 568/571 |
| 4,408,081 | 10/1983 | Foster | 568/571 |
| 4,408,082 | 10/1983 | Baumgartner | 568/571 |
| 4,455,440 | 6/1984 | Chiyoda | 568/571 |
| 5,767,322 | 6/1998 | Zakoshansky | 568/571 |
| B1 4,408,081 | 5/1986 | Foster et al. | 568/571 |

FOREIGN PATENT DOCUMENTS

| | | | |
|---|---|---|---|
| 0 399 776 A2 | 11/1990 | European Pat. Off. | C07C 409/08 |
| 0 416 744 A2 | 3/1991 | European Pat. Off. | C07C 407/00 |
| 0 567 336 A1 | 10/1993 | European Pat. Off. | C07C 409/04 |
| 0 584 956 A2 | 3/1994 | European Pat. Off. | C07D 301/19 |

*Primary Examiner*—Gary Geist
*Assistant Examiner*—Jean F Vollano

[57] ABSTRACT

The invention relates to a process for preparing organic hydroperoxides by oxidation of a hydrocarbon feed with molecular oxygen at supercritical conditions, which process is carried out in the presence of a separate liquid water phase that is present in an amount of 0.5 to 20% weight on the weight of the feed as a water film on the inner walls of the reactor vessel.

12 Claims, No Drawings

PROCESS FOR PREPARING ORGANIC HYDROPEROXIDES

BACKGROUND OF THE INVENTION

The invention relates to a process for preparing organic hydroperoxides.

Processes for the preparation of organic hydroperoxides by oxidizing the corresponding hydrocarbons are known from U.S. Pat. Nos. 4,329,514; 4,404,406; 4,408,081; 4,408;082; European patents applications Nos. 584,956 and 567,336 and other documents. Tertiary-butyl hydroperoxide (TBHP) may be prepared this way, as well as hydroperoxides of cyclohexane, cumene and ethylbenzene. TBHP is of particular interest, as it can be used in the synthesis of propylene oxide (PO) and, via the intermediate tertiary butyl alcohol, of methyl tertiary-butyl ether (MTBE). An example of this synthesis is found in European patent application No. 416,744 and prior art discussed therein. The synthesis of organic hydroperoxides is not an easy one. Aside from (explosive) runaway reactions, also the lack of selectivity towards the desired organic hydroperoxide is an issue of major concern. A 100 percent yield is impossible due to the variety of oxidation reactions competing with each other. Besides, the yield is also affected by decomposition of the hydroperoxide. For instance, cumene hydroperoxide will decompose (rearrange) into phenol and acetone (cf. "Organic Chemistry" by Morrison and Boyd, 3rd ed., sec. 28.6). Similar reactions are known from "Advanced Organic Chemistry" by Jerry March, 3rd ed. (cf. reaction 8–23). This decomposition may be catalyzed by trace amounts of metal ions derived from the (chromium/steel) inner reactor walls (e.g., $Fe^{2+}$ and $Fe^{3+}$).

The first step as described in the art to improve the selectivity and reduce decomposition concerns treatment of the reactor walls, typically with sodium pyrophosphates as disclosed in U.S. Pat. No. 3,816,540, or with sodium stannate. Often the inner reactor walls are already passivated by the manufacturer prior to delivery. This method is effective, as removing the sodium pyrophosphates lowers the selectivity, which may be restored upon renewed passivation.

Another approach concerns the use of reactors that are entirely inert, such as, gold plated reactors. Increased selectivity's under comparable circumstances may be found. However, the prevailing reaction conditions will damage the gold plating, resulting in the loss of selectivity. As the manufacture and rejuvenation of gold plated reactors is highly expensive, this approach is not attractive.

Ideally the selectivity towards organic hydroperoxides is improved up to the rate achievable in a gold plated reactor, without the disadvantages mentioned above. This the inventors now have achieved with a relatively simple adaptation of known processes.

SUMMARY OF THE INVENTION

The invention provides a process for preparing organic hydroperoxides by oxidation of a hydrocarbon feed with molecular oxygen at supercritical conditions, which process is carried out in the presence of a separate liquid water phase that is present in an amount of 0.5 to 20% weight on the weight of the feed as a water film on the inner walls of the reactor vessel.

DETAILED DESCRIPTION OF THE INVENTION

The inventors found plain water to be able to shield the reactor walls, thereby preventing contact between the organic hydroperoxides and the reactor walls. Surprisingly, the decomposition is not brought about by metal ions transmigrating through the water film. Moreover, water and (Lewis) acids are known to catalyze the rearrangement of the organic hydroperoxides, which would have caused the skilled reader to believe more rather than less decomposition to occur.

Preferably, the water is present in an amount of 0.75 to 10% w/w, more preferably in an amount of 1.0 to 3.0% w/w.

The preservation of the water film depends on the geometry of the reaction vessel and the manner (rate) of stirring, and it may be affected by addition of water during the process. The proper form and location of the rotor blades as well as manner of stirring may be determined without difficulty in a limited number of experiments or through suitable computer design.

A further important variable is the density of the reaction mixture. For instance, the density of TBHP is lower than that of ethylbenzene hydroperoxide, making it easier to form a stable film to shield the inner reactor walls. The density of the reaction mixture may of course be varied through the use of solvents.

Contrary to passivation, the effect of enhanced selectivity does not continue indefinitely. If in the process the water film deteriorates due to water loss, as may occur in continuous reactions, then the water should be replenished. If not, a decrease in selectivity comparable to that of unpassivated reactor vessels may occur.

Moreover, mere addition of water does not suffice. If it does not form the separate phase that shields the inner reactor walls the outcome of the process will be quite different. For instance, European patent application No. 399,776, describes the production of acetophenone which is the decomposition product of ethylbenzene peroxide. In that production process the (direct) water addition rather increases the selectivity in favor of the decomposition product. The reason for this difference in behavior is likely caused by water dissolution in the product phase (at too low concentrations) and/or insufficient shielding of the inner reaction walls (at too high or too low stirrer speed, and/or too small a difference in density).

The process of the invention is used for the preparation of organic hydroperoxides from alkanes, aralkanes and cycloalkanes, although alcohols and aldehydes may also be used (thus preparing peracids and the like). However, the process should be conducted at supercritical conditions, whereas the critical temperature should preferably not exceed 250° C. The range of suitable starting compounds thus includes compounds such as (critical temperature in °C. in brackets): isobutane (134.7); isopentane (187.8); 2-methylpentane (224.3); cyclopentane (238.6) and isopropanol (235). Preparing hydroperoxides from such like as cyclohexane (280.4); ethylbenzene (343.9); cumene (362.7) and 2-ethylnaphthalene (513.3) will be difficult, but not impossible.

Preferably, the process is conducted below 200° C. Accordingly, the preferred starting compounds are isobutane and isopentane. Preferred reaction conditions are indicated in claims 5 and 6.

The present autoxidation reaction is carried out at supercritical conditions, i.e., at such pressure and temperature conditions, that the hydrocarbon feed forms neither a liquid phase nor a gaseous phase, but rather a single dense phase. In case of isobutane, the super-critical conditions require a pressure in excess of 36 bar and a temperature in excess of 135° C. Oxidation of isobutane under super-critical conditions has been described in U.S. Pat. No. 4,404,406, the contents of which is herewith incorporated by reference. Obviously, in case another feed is used different temperature and pressure conditions apply.

Autoxidations are generally carried out with a surplus of feed over molecular oxygen and with only little conversion of the feed to avoid competing reactions to occur and decomposition of the organic hydroperoxides. Typically, the conversion of the hydrocarbon feed is in the range of 1 to 25%, based on the hydrocarbon feed. More suitably, the conversion is in the range of 5 to 15%. Decomposition may also be avoided by addition to the reaction mixture of an inorganic base such as any one of the hydroxides, carbonates, bicarbonates, phosphates, or pyrophosphates of the alkali metals or earth alkaline metals and the alkali metals of organic carboxylic acids, or by addition of an organic base, such as dimethyl amine trimethylamine, triethylamine, dibutylamine, triethanolamine, piperidine, pyridine and tetraethylenepentamine. The manner and amount of addition is disclosed in U.S. Pat. No. 4,329,514, incorporated herein by reference.

The amount of oxygen may be in the range of 10 to 30% mole on mole of the feed although more or less may be used. A ratio of 13 to 20 mole/mole is preferred. The oxygen may be supplied as air or as concentrated oxygen, but the preferred source of oxygen is pure oxygen.

The process may be conducted batch-wise or in a continuous mode, either as a single reaction, or by conducting a plurality of such oxidation reactions. Such a process is for instance disclosed in U.S. Pat. No. 4,408,081, using a cascade of reactors. In case a cascade of reactors is used, preferably in at least the last reactor of the cascade water is present. Preferably, the process is conducted in a continuous manner, with residence times suitably in the order of 15 to 90 minutes, for instance in the order of 30 to 60 minutes. Residence times in batch reactors are comparable.

The invention is illustrated by the following example(s). The experiments are all carried out at the following standard process conditions: T=150° C., p=70 bar absolute, isobutane (IB) is used as feed in an IB/$O_2$ ratio of 15.3 mole/mole, a stirrer speed of 1000 RPM is used (not in Example 5) and the residence time is 45 minutes. Hence, the conditions applied are supercritical for IB.

EXAMPLE 1

A gold-plated reactor has been used to study the IB oxidation in a supposed absence of wall effects. The gold-plating included everything inside the reactor, so walls, inlet tubes and stirrer. The gold-plating was applied in a galvanic way.

In this reactor the selectivity turned about to be 76% mole. However, after two weeks of operation, the TBHP selectivity decreased. Upon opening of the reactor the gold plating showed several cracks.

EXAMPLE 2

Before the first experiment in a new "AISI 316" autoclave was performed, the 1 liter reactor was passivated overnight with a 2% w $Na_4P_2O_7$ aqueous solution at room temperature. After four months of operation, the TBHP selectivity was still 69% mole.

EXAMPLE 3

After four months of operation, the reactor was opened and cleaned (wiping with a tissue and rinsed with demineralized water, thereby removing the passivation). The blank experiment in absence of pyrophosphate provided a TBHP selectivity of 47% mole.

EXAMPLE 4

Subsequently, an experiment in absence of pyrophosphate was carried out, wherein water was continuously added (1% w on IB). A water film was formed. Surprisingly, this led to a strong increase in selectivity to 74% mole. After the addition was stopped, the selectivity returned to 47% mole. Resuming the continuous addition of 1% w water increased the selectivity again to 73% mole. After four months of operation, the TBHP selectivity was still 69% mole.

Comparison of these experiments illustrates the unexpected beneficial effect of the separate water layer shielding the reactor walls.

EXAMPLE 5

In this example the stirrer speed and direction have been varied. In absence of water, the stirrer speed does not influence the selectivity. However, in the presence of 3% w/w water, the TBHP/TBA ratio (w/w) increased from 2.8 to 3.6 with a stirrer speed going from 330 to 1180 rpm. At 330 rpm, the stirring direction also influences the TBHP/TBA ratio, but this is not the case at 1180 rpm. These experiments illustrate the importance of proper stirring conditions to achieve optimal selectivity.

We claim:

1. A process for preparing organic hydroperoxides by oxidation of a hydrocarbon feed with molecular oxygen at supercritical conditions, which process is carried out in the presence of a separate liquid water phase that is present in an amount of 0.5 to 20% weight on the weight of the feed as a water film on the inner walls of the reactor vessel.

2. A process as claimed in claim 1, wherein the water is present in an amount of 0.75 to 10% w/w.

3. A process as claimed in claim 1, wherein the water is present in an amount of 1.0 to 3.0% w/w.

4. A process of claim 1 wherein the hydrocarbon feed comprises isobutane or isopentane.

5. A process of claim 1 carried out at a pressure in the range of 2 to 100 bar.

6. A process of claim 5, carried out at a pressure of 10 to 90 bar.

7. A process of claim 6 carried out at a pressure in the range of of 30 to 80 bar.

8. A process of claim 1, carried out at a temperature in the range of 125 to 175° C.

9. A process of claim 7, carried out at a temperature in the range of 145 to 160° C.

10. A process of claim 1 wherein the hydrocarbon feed is isobutane, and a pressure in excess of 36 bar and a temperature in excess of 135° C. is used.

11. A process of claim 1 wherein the conversion of the hydrocarbon feed is 1 to 25%, based on the hydrocarbon feed.

12. A process of claim 1 wherein the amount of oxygen is 10 to 20% mole on mole of the hydrocarbon feed.

* * * * *